United States Patent [19]

Bellows

[11] Patent Number: 5,002,644
[45] Date of Patent: Mar. 26, 1991

[54] METHOD FOR MONITORING SULFATES AND CHLORIDES AT LOW CONCENTRATION

[75] Inventor: James C. Bellows, Maitland, Fla.
[73] Assignee: Westinghouse Electric Corp., Pittsburgh, Pa.
[21] Appl. No.: 469,980
[22] Filed: Jan. 25, 1990

Related U.S. Application Data

[63] Continuation-in-part of Ser. No. 429,110, Oct. 30, 1989, abandoned.
[51] Int. Cl.$^5$ ............................................ G01N 27/333
[52] U.S. Cl. ........................... 204/153.13; 204/153.19; 204/416; 204/419
[58] Field of Search ........... 204/153.1, 153.13, 153.14, 204/153.19, 416–419

[56] References Cited

U.S. PATENT DOCUMENTS 3,563,874 2/1971 Ross et al. ............................ 204/419
3,672,962 6/1972 Frant et al. .......................... 204/419

OTHER PUBLICATIONS

Durst, "Ion-Selective Electrodes", (1969), p. 101.
Orion Research, Analytical Methods Guide, (1972), pp. 4, 13, 14.

Primary Examiner—T. Tung

[57] ABSTRACT

A method for monitoring low anion concentrations, and particularly sulfate concentrations in aqueous solutions is provided which includes the steps of adjusting the pH of the solution to substantially reduce the presence of hydroxides therein, mixing a nonionic solvent with the solution selected from the group consisting of alcohols, aldehydes, ketones, nitriloes and other water soluble organic compounds which do not contain sulfonate groups, exposing the solution and solvent mixture to an electrode selective for sulfate ions, exposing the mixture to a counter electrode and measuring the difference in voltage across the electrodes. A chilling apparatus may be added to reduce solvent consumption and lower the detection limit.

43 Claims, 1 Drawing Sheet

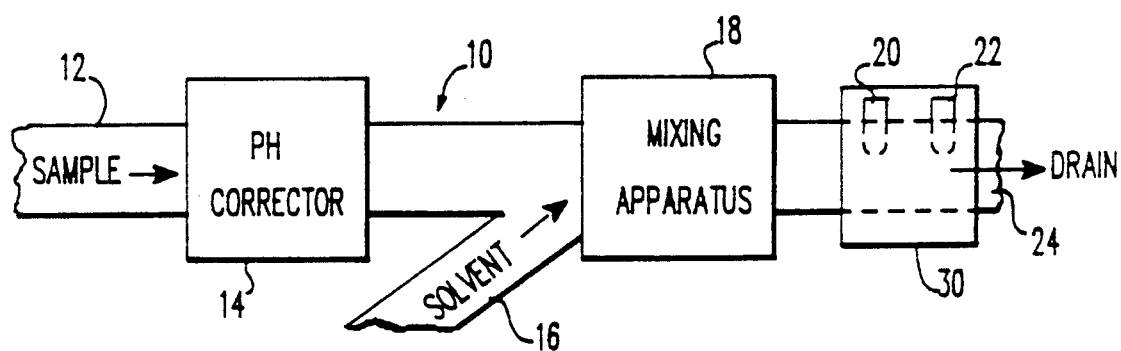

METHOD FOR MONITORING SULFATES AND CHLORIDES AT LOW CONCENTRATION

This is a continuation-in-part of a U.S. Ser. No. 429,110, filed Oct. 30, 1989, now abandoned.

BACKGROUND OF THE INVENTION

1. Field of the Invention

The present invention relates to electrochemical detection and measurement and more particularly to a method for monitoring sulfates in aqueous solutions. The method is general for reducing the detection limit of anion monitors which employ electrodes consisting of a metal and its sparingly soluble salt, such as a chloride monitor employing a silver-silver chloride electrode.

2. Description of the Prior Art

Sulfur containing materials are regularly used in industry. For example, sulfuric acid in high concentrations is used in the maintenance of power plant equipment such as the regeneration of demineralizes and condensate polishers.

In many cases it is important to remove all traces of sulfates from treated equipment and water streams. Conventional methods of monitoring ion concentrations to insure the removal of undesirable ions employ ion selective electrodes. For example, a conventional device for detecting chloride ions includes a sample inlet port, means for correcting the pH of the sample to prevent the electrodes from being affected by hydroxides which may have been present in the sample, a chloride ion selective electrode and a counter electrode to complete the circuit. Any chloride ions present in the sample will react with the ion selective electrode. The chemical potential of the reaction is measured via the difference in voltage across the electrodes. Knowledge of the potential permits calculation of the ionic concentration present in the sample.

Ross et al. U.S. Pat. No. 3,563,874 issued on Feb. 16, 1971 is exemplary of conventional ion selective electrodes.

When the solubility of the salt used in the anion selective electrode is such that the anion concentration due to electrode dissolution is much greater than the concentration of the anion in the sample, there are severe problems with measurement of the concentration of the anion. The solution to these problems is described here for a monitor based on a barium sulfate electrode, but the solution is applicable to any anion electrode where the salt is not adequately insoluble.

In detecting sulfate ions, barium with a barium sulfate coating would react with sulfates in a sample. However, an electrode coated with barium sulfate is not satisfactory for detecting trace amounts of sulfates in a sample because the barium sulfate is not completely insoluble. Water present in the sample dissolves barium sulfate. When the sample contains only trace amounts of sulfate, the dissolved barium sulfate from the electrode masks the real concentration of sulfates originally present in the sample. It may even prevent the determination of whether any sulfate was present in the sample. Thus, the degree of sensitivity of a barium sulfate coated electrode is very poor for low levels of sulfates. Unfortunately, concentrations of sulfate too small for detection by conventional methods are high enough to damage equipment.

It is an object of the present invention to provide a method for monitoring sulfate levels in aqueous solutions. It is a further object of the present invention to provide such a method which is sensitive to trace amounts anions such as sulfates.

SUMMARY OF THE INVENTION

The present invention provides an improved method for detecting and measuring low concentrations of anions, particularly sulfate, in aqueous solutions. The solution, if not already acid, must have its pH adjusted to substantially reduce the presence of hydroxides therein. The addition of effective amounts of an acid such as formic acid or acetic acid, will produce a solution having the desired pH. The method includes the further steps of adding to the solution, a predetermined amount of a nonionic solvent which is soluble in water at the operative temperature to form a mixture of the solution and the solvent, exposing the mixture to an electrode made of a material which is selective for sulfate ions, exposing the mixture to a counter electrode and measuring the difference in voltage across the electrodes.

The solvent is selected from the group consisting of alcohols, aldehydes, ketones, nitriles and other water soluble organic compounds containing 1 to 4 carbon atoms and which do not contain sulfonate groups. Ethanol and acetone are examples of satisfactory solvents.

The electrode is preferably made of barium having a barium sulfate coating. The counter electrode is preferably a normal calomel electrode.

The addition of the nonionic solvent to the aqueous solution dilutes the solution and thereby reduces solubility of barium sulfate which in turn is effective in reducing the rate of dissolution of the material of the sulfate electrode to prevent masking of sulfate from the solution by sulfate from the dissolved electrode material. The electrode and solution may also be refrigerated to further lower the solubility of the electrode material. Reducing or eliminating the dissolution of the electrode material permits the detection of heretofore undetectable trace amounts of sulfate when such sulfate is present in the solution.

BRIEF DESCRIPTION OF THE FIGURE

The present invention can be better understood by reference to the Figure which illustrates schematically a system in which the method of the present invention can be practiced.

DETAILED DESCRIPTION OF THE PREFERRED EMBODIMENT

The method of the present invention can be practiced in a system such as that illustrated in the Figure. The system 10 includes an inlet port 12 through which an aqueous solution enters and flows to a region 14 in which the pH of the solution is corrected or adjusted to a desired level by the addition of acids. System 10 also includes a solvent inlet port 16, mixing apparatus 18, an ion selective electrode 20 and a counter electrode 22. The solution exits through drain 24.

According to the preferred embodiment of the method of the present invention, an aqueous solution is introduced into inlet port 12. An effective amount of an acid, such as formic acid or acetic acid is added to the solution in region 14 to adjust the pH of the solution to 4 to 5 to substantially reduce the presence of hydroxides which, if present, would have an interference effect on the electrodes 20 and 22. If the solution is one which has been ascertained to be free of hydroxides initially, the pH adjustment may be unnecessary.

Thereafter, a solvent is added to the solution through inlet port 16. The solvent and solution are mixed by means of any suitable known mixing apparatus 18. The mixture formed from the solution and solvent is then exposed to the ion selective electrode 20 and then to the counter electrode 22. The ion selective electrode 20 is made of a material selective for the anion of interest. In the case of sulfate ions it is preferably barium and a barium sulfate coating. The counter electrode may be a conventional normal calomel electrode.

Other electrodes are lead with a lead sulfate coating, silver with a silver chloride coating, barium with a barium sulfate coating, and mercury with a mercurous chloride coating.

The solvent is any suitable nonionic solvent which is miscible with water at the operative temperature. The miscibility will vary somewhat with varying temperatures according to known relationships which are either published or approximately derived from well known chemical principles. The solvent is preferably selected from the group consisting of alcohols, aldehydes, ketones, nitriles and other water soluble organic compounds which do not contain functional groups related to the anion of interest, such as sulfonate. In order to maintain solubility, the organic compounds should contain relatively short chains of four or less carbon atoms. Specific examples are ethanol, acetaldehyde, acetone and acetonitrile.

The solvent facilitates the detection of even trace amounts of sulfates by reducing the dissolution of the ion selective electrode 20, attributable to the aqueous nature of the solution. The solvent reduces the rate of dissolution in two ways. The primary way is the effect of the solvent on the solubility product of the barium sulfate coating on electrode 20. A 30% solution of ethanol, for example, will reduce the solubility of barium sulfate by a factor of 20 by diluting the water in the solution.

The second way in which the solvent reduces the rate of dissolution of the electrode coating is by allowing the reduction of the temperature of the solution and the electrodes, preferably, below the normal freezing point of water, using chilling apparatus 30. Exposure of the solution and the electrode 20 to chilling apparatus 30 reduces solvent consumption and lowers the detection limit. For example, with a primarily aqueous solution the lower limit on temperature that can be achieved is essentially the freezing point of water, 32° F. By adding a solvent, such as ethanol, however, the freezing point of the solution, and thus the temperature to which the solution can be reduced, is much lower. For example, a mixture that contains 50 wt.% ethanol can be lowered to temperatures of about −40° F. without freezing.

The controlling factor in determining the percent by weight of solvent that should be added to the solution will be its effect on the solubility of the barium sulfate coating rather than the effect obtained by lowering the temperature of the solution. The optimal solvent/solution mixture ratio can be determined according to the following calculations. When an electrode of the second kind (metal in contact with its sparingly soluble salt), such as the barium sulfate electrode, is placed in a dilute solution of the anion of that salt, sulfate in this example, it develops a response that is given by the equation $$E = E^* + \frac{RT}{nF} \ln(X + Y)$$

where X is the concentration of anion due to the dissolution of the electrode material and Y is the concentration of anion in the original solution. In the present case, the anion is sulfate. By appropriate rearrangement, including expansion of the logarithm as a power series truncated after the linear term, this equation can be written in the form $$E = E' + \frac{RT}{nF} Y$$

provided that $Y >> X$ (for good results, Y is of the order of 0.1 X).

In order to have a 1 ppb sulfate value for Y, X must be approximately 100 ppb, which corresponds to a solubility product for $BaSO_4$ of $1 \times 10^{-12}$. This condition can be achieved at approximately 30% ethanol at 25° C. where the solubility of barium sulfate would produce 82 ppb sulfate. Alternatively, to reduce ethanol consumption, the ethanol could be reduced to 20% and the temperature lowered to approximately 0° C. Since the details of the particular barium sulfate electrode will also have some effect, only approximate values of the ethanol concentration and temperature can be given.

Because the dissolution of the barium sulfate coating on electrode 20 is responsible for masking the detection of any sulfate initially present in the solution, the addition of the solvent to reduce or eliminate the dissolution of the coating facilitates the detection of even trace amounts of sulfate.

Although the preceding discussion has used the example of sulfate measurement with a sulfate electrode, the method of adding a nonionic or non-aqueous solvent to the system to lower the solubility of the anion electrode material is general. The only real constraint is that the added solvent decreases rather than increases the solubility of the electrode material. For instance, ethanol would be an appropriate non-aqueous solvent for a silver-silver chloride electrode, but an amine (such as methyl amine) would not because it would complex with the silver and increase the solubility of the silver chloride from the electrode.

It is believed that far lower levels of sulfates and other anions can be detected by the method of the present invention than heretofore possible in a continuous monitor.

What is claimed is:

1. A method for monitoring sulfate concentrations in a generally acid aqueous solution comprising the steps of:
    adding to said solution a predetermined amount of a nonionic solvent which is soluble in water at an operative temperature to form a mixture of said solution and said solvent;
    exposing said mixture to an electrode made of a material which is selective for sulfate ions;
    exposing said mixture to a counter electrode; and
    measuring the difference in voltage across said electrodes;
    whereby said solvent reduces the rate of dissolution of said material of said electrode to prevent the masking of sulfate from said solution by sulfate from said dissolved material and thereby permits the detection of trace amounts of sulfate when such sulfate is present in said solution.

2. The method recited in claim 1 wherein said solvent is selected from the group consisting of alcohols, aldehydes, ketones, nitriles and other water soluble organic compounds which do not contain sulfonate groups, which contain one to four carbon atoms.

3. The method recited in claim 1 wherein said electrode is made of barium with a barium sulfate coating.

4. The method of claim 1 further comprising the step of refrigerating said electrode and said solution to further lower the solubility of said electrode material.

5. The method of claim 4 wherein the temperature of said electrode and said solution is lowered to below the normal freezing point of water.

6. The method recited in claim 1 wherein said electrode is made of lead with a lead sulfate coating.

7. The method recited in claim 6 wherein said solvent is ethanol.

8. A method for monitoring sulfate concentrations in aqueous solutions comprising the steps of:

adjusting the pH of an aqueous solution to substantially reduce the presence of hydroxides therein;

mixing with said solution a predetermined amount of a nonionic solvent which is soluble in water at an operative temperature to form a mixture of said solution and said solvent;

exposing said mixture to an electrode made of a material which is selective for sulfate ions;

exposing said mixture to a counter electrode; and measuring the difference in voltage across said electrodes;

whereby said solvent reduces the rate of dissolution of said material of said electrode to prevent the masking of sulfate from said solution by sulfate from said dissolved material and thereby permits the detection of trace amounts of sulfate when such sulfate is present in said solution.

9. The method recited in claim 8 wherein said solvent is selected from the group consisting of alcohols, aldehydes, ketones, nitriles and other water soluble organic compounds which do not contain sulfonate groups, which contain one to four carbon atoms.

10. The method recited in claim 7 wherein said electrode is made of barium with a barium sulfate coating.

11. The method of claim 8 further comprising the step of refrigerating said electrode and said solution to further lower the solubility of said electrode material.

12. A method for monitoring sulfate concentrations in aqueous solution comprising the steps of:

adjusting the pH of an aqueous solution by adding thereto an effective amount of an acid to substantially reduce the presence of hydroxides in said solution;

diluting said solution with a predetermined amount of a nonionic solvent which is soluble in water at an operative temperature;

mixing said solution and said solvent to form a mixture thereof;

exposing said mixture to an electrode made of a material which is selective for the sulfate ions;

exposing said mixture to a counter electrode;

measuring the difference in voltage across said electrodes;

whereby said solvent reduces the rate of dissolution of said material of said electrode to prevent the masking of sulfate from said solution by sulfate from said dissolved material and thereby permits the detection of trace amounts of sulfate when such sulfate is present in said solution.

13. The method recited in claim 12 wherein said solvent is selected from the group consisting of alcohols, aldehydes, ketones, nitriles and other water soluble organic compounds which do not contain sulfonate groups, which contain one to four carbon atoms.

14. The method recited in claim 12 wherein said electrode is made of barium with a barium sulfate coating.

15. The method of claim 12 further comprising the step of refrigerating said electrode and said solution to further lower the solubility of said electrode material.

16. The method of claim 15 wherein the temperature of said electrode and said solution is lowered to below the normal freezing point of water.

17. The method recited in claim 12 wherein said counter electrode is a calomel electrode.

18. The method recited in claim 12 wherein said acid is formic acid.

19. The method recited in claim 12 wherein said acid is acetic acid.

20. The method recited in claim 12 wherein said solvent is ethanol.

21. The method recited in claim 12 wherein said solvent is acetone.

22. The method recited in claim 12 wherein said solvent is acetaldehyde.

23. The method recited in claim 12 wherein said solvent is acetonitrile.

24. A method for monitoring chloride ion concentration in a generally acid aqueous solution comprising the steps of:

adding to said solution a predetermined amount of a nonionic solvent which is soluble in water at an operative temperature to form a mixture of said solution and said solvent;

exposing said mixture to an electrode made of a material which is selective for chloride ions;

exposing said mixture to a counter electrode; and measuring the difference in voltage across said electrode;

whereby said solvent reduces the rate of dissolution of said material of said electrode to prevent the masking of said chloride ions from said solution by anions from said dissolved material and thereby permits the detection of trace amounts of chloride ions when such chloride ion is present in said solution.

25. The method recited in claim 24 wherein said solvent is selected from the group consisting of alcohols, aldehydes, and ketones, which contain one to four carbon atoms.

26. The method recited in claim 24 wherein said electrode is made of silver and a silver chloride coating.

27. The method recited in claim 24 wherein said electrode is made of mercury with a mercurous chloride coating.

28. The method of claim 24 further comprising the step of refrigerating said electrode and said solution to further lower the solubility of said electrode material.

29. The method of claim 28 wherein the temperature of said electrode and said solution is lowered to below the normal freezing point of water.

30. A method for monitoring chloride ion concentration in aqueous solutions comprising the steps of:

adjusting the pH of an aqueous solution to substantially reduce the presence of hydroxides therein;

mixing with said solution a predetermined amount of nonionic solvent which is soluble in water at an operative temperature to form a mixture of said solution and said solvent;

exposing said mixture to an electrode made of a material which is selective for chloride ions;

measuring the difference in voltage across said electrodes;

whereby said solvent reduces the rate of dissolution of said material of said electrode to prevent the masking of said chloride ions from said solution by anions from said dissolved material and thereby permits the detection of trace amounts of chloride ions when such chloride ion is present in said solution.

31. The method recited in claim 30 wherein said solvent is selected from the group consisting of alcohols, aldehydes, and ketones, which contain one to four carbon atoms.

32. The method of claim 30 further comprising the step of refrigerating said electrode and said solution to further lower the solubility of said electrode material.

33. A method for monitoring chloride ion concentration in aqueous solution comprising the steps of:

adjusting the pH of an aqueous solution by adding thereto an effective amount of an acid to substantially reduce the presence of hydroxides in said solution;

diluting said solution with a predetermined amount of a nonionic solvent which is soluble in water at an operative temperature;

mixing said solution and said solvent to form a mixture thereof;

exposing said mixture to an electrode made of a material which is selective for chloride ions;

exposing said mixture to a counter electrode; and measuring the difference in voltage across said electrodes;

whereby said solvent reduces the rate of dissolution of said material of said electrode to prevent the masking of chloride ions from said solution by anions from said dissolved material and thereby permits the detection of trace amounts of chloride ions when such chloride ion is present in said solution.

34. The method recited in claim 33 wherein said solvent is selected from the group consisting of alcohols, aldehydes, and ketones, which contain one to four carbon atoms.

35. The method of claim 33 further comprising the step of refrigerating said electrode and said solution to further lower the solubility of said electrode material.

36. The method of claim 35 wherein the temperature of said electrode and said solution is lowered to below the normal freezing point of water.

37. The method recited in claim 33 wherein said counter electrode is a calomel electrode.

38. The method recited in claim 33 wherein said acid is formic acid.

39. The method recited in claim 33 wherein said acid is acetic acid.

40. The method recited in claim 33 wherein said solvent is ethanol.

41. The method recited in claim 33 wherein said solvent is acetone.

42. The method recited in claim 33 wherein said solvent is acetaldehyde.

43. The method recited in claim 33 wherein said electrode is made of silver with a silver chloride coating.

* * * * *